United States Patent [19]
Molina; Jose Luis, H. D.

[11] Patent Number: 5,460,650
[45] Date of Patent: Oct. 24, 1995

[54] PROCESS FOR PREPARING A TRAUMATOLOGICAL PLASTERING WITH DAMP-PROOF AND HARD-WEARING PROPERTIES

[75] Inventor: Jose Luis, H. D. Molina, Cordoba, Spain

[73] Assignee: Soymo, S.A., Cordoba, Spain

[21] Appl. No.: 328,290

[22] Filed: Oct. 21, 1994

Related U.S. Application Data

[63] Continuation-in-part of Ser. No. 33,408, Mar. 17, 1993, abandoned.

[30] Foreign Application Priority Data

Mar. 18, 1992 [ES] Spain .................................... 9200591

[51] Int. Cl.⁶ .................................................. C04B 11/00
[52] U.S. Cl. ............................................. 106/772; 602/8
[58] Field of Search .................................. 106/772; 602/8

[56] References Cited

U.S. PATENT DOCUMENTS

| | | | |
|---|---|---|---|
| 3,316,901 | 5/1967 | Smith | 602/8 |
| 3,415,243 | 12/1968 | Sheldon | 602/8 |
| 3,490,445 | 1/1970 | Laakso | 602/8 |
| 3,785,373 | 1/1974 | Smith | 602/8 |
| 3,944,425 | 3/1976 | Magder | 106/681 |
| 4,136,687 | 1/1979 | Dabroski | 602/8 |
| 4,320,750 | 3/1982 | Dabroski | 602/8 |

FOREIGN PATENT DOCUMENTS 0561407  9/1993  European Pat. Off. .

Primary Examiner—Mark L. Bell
Assistant Examiner—Michael Marcheschi
Attorney, Agent, or Firm—Peter L. Michaelson; Jeffery J. Brosemer

[57] ABSTRACT

A method for obtaining a traumatologic plastering with damp-proof and hard-wearing properties consisting of adding to a volume of one liter of containing product 96 through 99% of warm water having a value of 7.65 pH, the following components being added to obtain 1 liter of this product: 43 mg of Sodium, 7.30 mg of Potassium, 8.02 mg of Calcium, 1.20 mg of Magnesium, 0.40 mg of Americium, 580 mg of Nitrate, 0.53 mg of Nitrite, 25.6 mg of Sulfate, <0.004 mg of Cyanide, <0.05 mg of Phosphorus, <0.05 mg of Iron, <0.06 mg of Manganese, <0.05 mg of Copper, and <0.10 mg of Aluminum, the inorganic elements constituting a fluid or powdered mixture if not dissolved in water.

2 Claims, No Drawings

PROCESS FOR PREPARING A TRAUMATOLOGICAL PLASTERING WITH DAMP-PROOF AND HARD-WEARING PROPERTIES

CROSS-REFERENCE TO RELATED APPLICATION

This is a continuation-in-part application of my United States patent application Ser. No. 08/033,408, filed on Mar. 17, 1993 now abandoned.

BACKGROUND OF THE INVENTION

The present specification refers to a patent invention relating to a method for obtaining a traumatological plastering with damp-proof and hard wearing properties, the evident purpose of which is to allow a traumatologic plastering to be obtained from the achievement of its method.

1. Field of the Invention

The application of this invention is found in the industry devoted to medicine and similar.

2. Related Art

The gypsum or hydrated calcium sulfate is the most common of sulfates, stemming above all from the seawater evaporation, its crystals adopting varied shapes.

Plaster is a fine gypsum obtained by cooking crude gypsum at a temperature of 120° C.

The use of gypsum and plaster is a very utilized method for immobilizing body segments showing bony injuries, specially fractures.

Although it is known the existence of this very old use of this therapeutic method, it is only, nevertheless, from 1830 that the present plastering method is used, which is constituted by a bandage on which a smooth layer of gypsum or plaster is spread.

Plasterings are made on the basis of very varied methods, the most usual method being a circular bandage with plastered strips after being dipped in warm water.

Some bandages are wrapped in a rapid sequence around the corporal segment to be immobilized, after being modeled.

After a lapse of a few minutes the gypsum "sets" and becomes stiff.

The gypsum remains in situ for a period of 20 through 40 days, even more, in accordance with the orthopaedic requirements, until an osseous corn is formed at the level of the fracture. Lastly, the gypsum is removed by an adequate method.

Different methods of therapeutic plastering have introduced slight differences with regard to the described general method.

In any case, all the known methods have as a negative common denominator the fact that they do not withstand a continuous contact with water, since gypsum and plaster proceeding originally from evaporation and dehydration when in contact with water lose essentially one of their main characteristics and advantages, such as their consistence and hardness, so that the present traumatologic plasterings cannot contact the water at all.

Comparably, other negative characteristic of these traumatologic plasterings observed in the state of the art is their limited shock resistance, given that they can totally or partially break with a relative easiness.

An evident solution to the present problems in this matter would be to rely on a plastering resolving both negative characteristics, obtaining, on the contrary, a traumatologic plastering having damp-proof and hard-wearing properties.

Nevertheless, until now, nothing is known on the existence of a plastering having characteristics which could be denominated as suitable.

SUMMARY OF THE INVENTION

The method for obtaining a traumatological plastering with damp-proof and hard-wearing properties as proposed by the invention constitutes per se an evident solution to the present problem on this matter, since starting from its utilization, it has been introduced the novelty and the substantial advantage that the plastering can be got wet, being fully water resistant in general, that is to say, it can withstand rainwater, the shower water and even the bath water, and it can contact the water without any disintegration, separation or loosening of material.

The method for obtaining a traumatological plastering with damp-proof and hard wearing properties is based on the traditional methods of obtaining gypsum and plaster for TRAUMATOLOGICAL uses, with the supplementary utilization of special products modifying the molecular structure in gypsum and plasters to be transformed into more resistant damp-proof materials having a greater surface hardness, into special products which can be liquid, in which case they are poured into the mixed or impregnated water of the self-supporting bandages of plaster, or they can be solid and then they are incorporated milled together with the plaster powder.

This method also gives a greater resistance and hardening to the plastering, so allowing this to have a smaller section and requiring a smaller amount of material, both with regard to the bandage and the plaster in which the bandage is impregnated.

An additional advantage of the invention is that it means homogeneity in the results and a simplicity in all the process, the elaboration of the plastering not being substantially modified.

Its utilization is specially thought for traumatological plastering both of medical and veterinary use.

DETAILED DESCRIPTION OF THE INVENTION

The method for obtaining a traumatological plastering with damp-proof and hard-wearing properties is configured starting from the use of fine gypsum or plaster, said method being traditionally employed in traumatological applications, both of medical and veterinary use, with which, in its first preparation phase, the method of the invention fully coincides with the already known traditional methods.

The differential point from which the novelty and innovation start lies in the fact that when setting the plastered bandage in water, this operation of introduction in a liquid is carried out on the liquid product containing the special products in perfectly calculated amounts, which are water dispersed in the proportions shown in the abstract, or solid products in a powder which would be previously mixed with gypsum or plaster and later incorporated in the bandage. At the moment of using the bandage, this would be previously immersed in warm water and the products incorporated in the gypsum or plaster of the bandage would then act immediately.

The plastered bandage or plastered strips already treated are normally applied by wrapping in a rapid sequence the corporal segment to be immobilized. From this moment on, a chemical reaction is created which avoids the gypsum or plaster to crystallize, since it expels a great portion of the water retaining the mass.

The reactions produced imply a true change in the molecular structure of the gypsum or plaster, these materials acquiring, among other properties, a better surface hardness and a different hydrotermic performance, avoiding a continuous exchange of humidity with the environment and the contacting materials.

The gypsum and plaster so treated, once set, exhibit damp-proof and hard-wearing properties giving the user or patient two great positive advantages.

The first advantage offered by a gypsum and plaster bandage so treated is normal hygiene which is comparable with that other perfectly healthy person in that he/she will be able to have a shower or bath, immersing freely the plastered member or corporal segment without being afraid of losing the plastering when entering the water and remaining immersed in it, because a disintegration, separation or loosening process of the material, such as it happens today with the previously known traumatologic plasterings mentioned in the specification in the section corresponding to the related art or The state of the art.

Second, when the plastering has a smaller section, it is evident that the weight of same is substantially lesser than that a conventional plastering of those known up to date, with which the plastered member or corporal segment has, as until now, a total immobilization, while, on the other side, upon disposing of a smaller section, its limitations are noticeably reduced, with which the general motor function of the subject is increased.

These two advantages, i.e. the possibility of keeping a normal hygiene allowing the member or corporal segment to be immersed in water both for having a shower, or a bath, and for keeping a normal hygiene, and the fact that the plaster weight is substantially reduced, are totally innovative, and consequently determine a great progress in the traumatology field and the medicine in general, both from the point of view of therapeutics and traumatology and from the own comfort, or if desired, a minor suffering and limitations of the person treated with the therapeutic method contemplated in this traumatologic plastering.

The present invention configuring a method for obtaining a traumatologic plastering with damp-proof and hard-wearing properties, is an absolute innovation in the medicine field, since at present, there is no method furnishing the properties and innovations referred to in the present invention.

In synthesis, this invention provides a method for obtaining a traumatologic gypsum bandage having damp-proof and hard-wearing properties, which configures as follows:

For obtaining one liter of the product within which an immersion of the bandages to be later applied on the fractured member or corporal segment is to be effected, said liter of product will be composed of an amount of warm water on the order of 96 and 99%, this water having a value of 7.65 pH, there being inside the liquid configured by the warm water a dried residue on the order of 696 through 699 mg, which is composed of metallic salts comprising 43 mg of Sodium, 7.30 mg of Potassium, 8.02 mg of Calcium, 1.20 mg of Magnesium, 0.40 mg of Americium, 580 mg of Nitrate, 0.53 mg of Nitrite, 25.6 mg of Sulfate, < 0.004 mg of Cyanide, <0.05 mg of Phosphorous, <0.05 mg of Iron, <0.06 mg of Manganese, <0.05 mg of Copper, and <0.10 mg of Aluminum, according to which the inorganic elements can consist of a fluid or powdered mixture if not water dissolved.

One of the preferred methods, such as previously mentioned, is configured by introducing the plastered bandages in said fluid mixture and the bandages, once wetted in this liquid provided with the above-mentioned products, are squeezed out and then applied, wet, around the damaged member or corporal part.

It is not considered necessary to extend more this description for an expert in the art to understand the scope of the invention and the advantages derived from it.

The term under which this specification has been described should be always taken in an ample and non-limitative sense.

I claim:

1. A process for the preparation of a traumatologic plastering composition having damp-proof and hard-wearing properties which comprises the steps of admixing a containing product selected from the group consisting of gypsum and plaster, with from 960–990 milliliters of warm water having a pH of 7.65 and a dried residue of from 696–699 milligrams comprising
    (a) 43 milligrams of Sodium,
    (b) 7.30 milligrams of Potassium,
    (c) 8.02 milligrams of Calcium,
    (d) 1.20 milligrams of Magnesium,
    (e) 0.40 milligrams of Americium,
    (f) 580 milligrams of a Nitrate,
    (g) 0.53 milligrams of a Nitrite,
    (h) 25.6 milligrams of a Sulfate,
    (I) <0.004 milligrams of Cyanide,
    (j) <0.05 milligrams of Phosphorous,
    (k) <0.05 milligrams of Iron,
    (l) <0.06 milligrams of Manganese,
    (m) <0.05 milligrams of Copper, and
    (n) <0.10 milligrams of Aluminum,
and continuing the admixing until the dried residue is homogenized in the liquid.

2. Process in accordance with claim 1 comprising the additional step of applying the homogenized liquid gypsum mixture to plaster bandages which are subsequently immersed with warm water.

* * * * *